(12) United States Patent
Theoharides

(10) Patent No.: US 6,984,667 B2
(45) Date of Patent: Jan. 10, 2006

(54) SYNERGISTIC PROTEOGLYCAN COMPOSITIONS FOR INFLAMMATORY CONDITIONS

(75) Inventor: Theoharis C. Theoharides, Brookline, MA (US)

(73) Assignee: Theta Biomedical Consulting and Development Co., Brookline, MA (US)

( * ) Notice: Subject to any disclaimer, the term of this patent is extended or adjusted under 35 U.S.C. 154(b) by 183 days.

(21) Appl. No.: 09/771,669

(22) Filed: Jan. 30, 2001

(65) Prior Publication Data

US 2002/0176902 A1 Nov. 28, 2002

Related U.S. Application Data

(63) Continuation-in-part of application No. 09/056,707, filed on Apr. 8, 1998, now Pat. No. 6,689,748.

(51) Int. Cl.
 *A61K 7/16* (2006.01)
 *A61K 9/20* (2006.01)
 *A01N 25/00* (2006.01)

(52) U.S. Cl. .............. 514/886; 424/49; 424/464; 514/887; 514/901

(58) Field of Classification Search ............... 424/400, 424/439, 451, 464, 59; 514/825, 886
See application file for complete search history.

(56) References Cited

U.S. PATENT DOCUMENTS

| | | | | | |
|---|---|---|---|---|---|
| 5,223,257 A | * | 6/1993 | Arora | ............... | 424/742 |
| 5,804,594 A | * | 9/1998 | Murad | ............... | 514/474 |
| 6,136,795 A | * | 10/2000 | Florio | ............... | 514/62 |

* cited by examiner

*Primary Examiner*—Thurman K. Page
*Assistant Examiner*—S. Howard
(74) *Attorney, Agent, or Firm*—Law Office of Dr. Melvin Blecher

(57) ABSTRACT

Compositions with synergistic anti-inflammatory effect in inflammatory diseases resulting from activation and consequent degranulation of mast cell and followed by secretion of inflammatory biomolecules from the activated mast cells, composed of a heavily sulfated, non-bovine proteoglycan such as chondroitin sulfate C and one or more of a hexosamine sulfate such as D-glucosamine sulfate, a flavone such as quercetin, a special organic extra virgin kernel seed olive oil, S-adenosylmethionine and diphenhydramine.

27 Claims, No Drawings

SYNERGISTIC PROTEOGLYCAN COMPOSITIONS FOR INFLAMMATORY CONDITIONS

This is a continuation-in-part/application based on U.S. Ser. No. 09/056,707, filed Apr. 8, 1998, now U.S. Pat. No. 6,689,748.

The invention is generally related to the treatment of inflammatory conditions. More specifically, the invention is related to compositions containing inhibitors of mast cell activation and secretion designed to be used as dietary supplement in the treatment of inflammatory conditions.

There have been a number of mostly anecdotal reports that the proteoglycan chondroitin sulfate, as well as glucosamine sulfate, a product of the intestinal breakdown of proteoglycans may be helpful in relieving the pain of osteoarthritis:—Shute N. Aching for an arthritis cure. *US News and World Report*, Feb. 10, 1997.—Cowley G. The arthritis cure? *Newsweek*, Feb. 17, 1997.—Foreman J. People, and their pets, tout arthritis remedy. *The Boston Globe*, Apr. 7, 1997; Tye L. Treatment gains scientific attention. *The Boston Globe*, Sep. 25, 2000.

A recent meta-analysis showed potential therapeutic benefit of chondroitin sulfate in osteoarthritis [McAlindon et al. *J Am Med Assn.* 283:1469 (2000), and NIH-funded clinical trial OD-98-003 dated Oct. 10, 1997]. However, less than 5% of the chondroitin sulfate in available preparations is absorbed orally. Furthermore, such commercial preparations use chondroitin sulfate obtained from cow trachea, with the possible danger of contracting "mad cow disease" [McAlindon et al. above]. In fact, the European Union has banned even cosmetics that contain bovine-derived products.

Theoharides et al., *British Journal of Pharmacology* 131:1039, (2000) indicated for the first time how proteoglycans such as chondroitin sulfate may work. The paper reported that chondroitin sulfate and, to a lesser degree, glucosamine sulfate, inhibit activation of mast cells that are known to trigger allergy and asthma. Mast cells are also now recognized as important causative intermediary in many painflul inflammatory conditions[Galli, *N Eng J Med.* 328:257 (1993); Theoharides, *Int J Tissue Reactions* 18:1 (1996)], such as insterstitial cystitis and irritable bowel syndrome [Theoharides, *Ann NY Acad, Sci.* 840:619 (1998)], as well as in migraines and possibly multiple sclerosis [Theoharides, *Persp Biol Med.* 26:672 (1983); Theoharides, *Life Sci* 46:607 (1996)]. In fact, glucosamine was recently considered to be prophylactic for migraines [Russell, *Med Hypoth* 55:195 (2000)].

Mast cells are increasingly implicated in conditions involving inflamed joints, such as in rheumatoid arthritis, through activation of local mast cells by, for example, neuropeptides. Additional indirect evidence also supports the involvement of mast cells in bone resorption: (a) systemic mastocytosis is invariably associated with osteoporosis; (b) inhibition of mast cell mediator release reversed lytic bone changes; (c) depletion of mast cells inhibited bone resorption in organ culture; (d) human synovial mast cells were shown to secrete in response to allergic and non-immunologic stimuli; (e) human mast cells release the cytokine IL-6 and (f) IL-6 has been definitively linked to bone resorption and osteoporosis.

It was recently shown that chondroitin sulfate's ability to inhibit the activation of mast cells is synergistic with the inhibitory effects on mast cell activation of another class of naturally occurring compounds, the flavonoids [Middleton et al. *Pharm Rev* 52:1 (2000)]. Certain plant flavones (in citrus fruit pulp, seeds, sea weed) are now recognized as anti-allergic, anti-inflammatory, anti-oxidant and cytoprotective with possible anti-cancer properties. Only some flavones, such as quercetin, inhibit mast cell activation and inflammatory cells.

Quercetin inhibits secretion from human activated mast cells [Kimata et al. *Allergy*30:501(2000)], and has also been used effectively for the treatment of chronic prostatitis [Shoskes et al., *Urology*54:960 (1999)]. Other flavonoids may have opposite effects. Use of the term "bioflavonoids" listed in certain commercial products, therefore, provides little information, and may include molecules that have detrimental effects.

Copending U.S. patent application Ser. No. 09/056,707, filed Apr. 8, 1998, claims the use of proteoglycans, without and with flavonoids, for the treatment of mast cell activation-induced diseases. The information contained therein is incorporated by reference into the present application.

An important need therefore exists for dietary formulations suitable for human patients that are synergistic in that they have stronger effects than the sum of the effects of the individual components, and also synergistic with standard clinical treatments of inflammatory conditions, such as osteoarthritis. "Synergistic" is intended to mean: "coordinated or correlated action by two or more structures or drugs" [Stedman's Medical Dictionary,23rd edition, Williams & Wilkins, Baltimore, 1976]. Such formulations have been discovered, and are described below.

SUMMARY OF THE INVENTION

The invention comprises compositions for human use containing a sulfated proteoglycan and one or more active ingredients selected from the group consisting of a sulfated hexosamine, a flavonoid compound ("flavone"), an organic virgin kernel seed olive oil, S-adenosylmethionine and diphenhydramine, together with appropriate excipients and carriers, said compositions having improved absorptivity from the gastrointestinal tract and anti-inflammatory effects synergistic with each other and synergistic with standard clinical treatment modalities.

In one embodiment, the proteoglycan is non-bovine chondroitin sulfate, the sulfated hexosamine is D-glucosamine sulfate, the flavone is quercetin, and the kernel seed olive oil is extra virgin (first pressing, no heat, no refining)).

In another embodiment, the compositions are enriched with omega fatty acids and alpha tocopherol.

DETAILED DESCRIPTION OF THE PREFERRED EMBODIMENTS OF THE INVENTION

It has been discovered that a combination of a sulfated proteoglycan, a sulfated D-hexoseamine and a flavone, along with an organic extra virgin kernel seed olive oil, has synergistic anti-inflammatory effects when used as a dietary supplement, without or with a conventional clinical treatment for inflammatory diseases. Such inflammatory diseases result from the activation, degranulation and consequent secretion of inflammatory biochemicals from mast cells, and the resultant inflammatory diseases include the group consisting of: osteoarthritis, cancer, fibromyalgia, inflammatory bowel disease, interstitial cystitis, irritable bowel syndrome, migraines, angina, chronic prostatitis, eczema, arthritis, multiple sclerosis, psoriasis, sun burn, and periodontal disease of the gums.

In a highly preferred embodiment, the sulfated proteoglycan is non-bovine chondroitin sulfate which blocks mast cell activation, degranulation and consequent secretion of inflammatory biochemicals from the mast cells. Other natural sulfated proteoglycans suitable for practicing this invention include keratan sulfate, dermatan sulfate and hyaluronic acid. The preferred biological source of the chondroitin sulfate is shark cartilage which is more-highly sulfated than the standard commercial chondroitin sulfate isolated from cow trachea.

The highly preferred flavone is quercetin which inhibits secretion of inflammatory molecules from mast cells by affecting moesin, a unique 78 kDa mast cell protein [Theoharides et al. *J Pharm Exp Therap* 294:810 (2000)]. In addition to quercetin, other flavones suitable in carrying out the invention include myrisetin, genistein and kaempferol.

The olive oil component of the inventive compositions is preferably an organic (no artificial fertilizers, no pesticides, no insectisides) extra virgin (first pressing, no heat, not refined) kernel seed olive oil produced on the island of Crete in Greece. This olive oil increases absorption of the other ingredients of the anti-inflammatory compositions, and also adds its own content of important anti-oxidants [Bosku, *World Rev Nutr Diet*, 87:56 (2000)], such as omega fatty acids and alpha tocopherol. Although not claimed herein, it has been claimed that kernel seed olive oil has cytoprotective, longevity-producing effects [Trichopoulou et al. *Am J Clin Nutr* 61:1346S (1995); Trichopoulou et al, *Cancer Epid Biomarker Prevention* 9:869 (2000)]. A source of the highly preferred extra virgin kernel seed olive oil is: E.B.E.K., Inc., Commercial, Industrial Enterprises of Crete, 118 Ethnikis Antistasecos, Heraklion, Crete, 71306, Greece.

Supplementation of the compositions described above with the methylation reagent S-adenosylmethionine ("SAM") adds antioxidant, anti-inflammatory and cytoprotective properties, particularly in inflammatory joint diseases. Another supplement to the basic compositions of the invention is diphenhydramine.

The preferred concentration range of the proteoglycan, hexosamine sulfate and flavone components of the oral formulations are 10–3,000 mg per tablet or capsule. The preferred concentration range for S-adenosylmethionine is 3–1,000 mg per capsule or tablet. Generally, where present, the amounts of the olive oil are at least three times those of the other active ingredients. The number of capsules or tablets to be taken per day is determined by the nature and severity of the medical condition, and is readily determinable by the patient's physician. Other representative formulations are described in the examples below.

The compositions of the invention may be formulated in any standard means of introducing pharmaceuticals parenterally into a patient, e.g., by means of tablets or capsules. The compositions of the invention include salves and creams for skin conditions, and mouth washes and toothpaste for periodontal diseases. Standard excipients and carriers for the active ingredients of the inventive compositions are described in Remington's Pharmaceutical Sciences, Mack Publishing Co., Easton, Pa.

Although not bound by any particular mechanism of action of the components of the claimed compositions, the inventor contemplates that the proteoglycan inhibits the activation and degranulation of the relevant mast cells, while the flavone inhibits the secretion of inflammatory biomolecules from these mast cells. "Activation" and "degranulation" of mast cells are defined herein as is standard and well known in this art.

EXAMPLES

Example 1

Table 1 compares chondroitin sulfate-containing commercial products to the present compositions.

TABLE 1

Comparison of Chondroitin Sulfate-Containing Products to Present Invention

| Product | Most Available Compositions | Present Invention |
|---|---|---|
| Main ingredient | Mixture of chondroitin sulfates | Chondroitin sulfate C |
| Source | Cow trachea | Shark cartilage |
| Amount per capsule or tablet | 150 mg | 10–3000 mg |
| Degree of sulfation | Low | High |
| Absorption from g.i. tract | <5% | >15% |
| Target | Unknown | Mast cells, bone cells |
| Other ingredients | Vitamins, fish oils (some preparations) | Flavones, omega-fatty acids, alpha-tocopherol, kernel olive seed oil, SAM |
| Advantages | None known | Anti-allergic, anti-inflammatory, anti-oxidant, cytoprotective |
| Adverse effects | Risk of mad cow disease, stomach upset, allergy to fish products | None known |
| Relevant conditions | Osteoarthritis | Angina, arthritis, chronic prostatitis, eczema, fibromyalgia, interstitial cystitis, irritable bowel syndrome, inflammatory bowel disease, migraines multiple sclerosis, psoriasis, periodontal disease. |
| Scientific publications | None found | Theoharides et al. Br J Pharm 131:1039 (2000) Middleton et al. Pharm Rev 52:673 (2000) |

Example 2

Composition of Formulation One (ALGONOT-PLUS, Registered Mark)

Dietary Supplement

Two capsules to be taken twice daily, at least one hour before meals

| Active ingredients: | |
|---|---|
| Chondroitin sulfate | 300 mg |
| D-Glucosamine sulfate | 300 mg |
| Quercetin | 300 mg |
| extra virgin kernel seed olive oil | 900 mg |

Hypo-allergenic, free from: artificial colors or flavors, corn, milk products, preservatives, salt, starch, sugar, wheat or yeast.

Example 3

Composition of Formulation Two (ALGONOT-PREVENT, Registered Mark)

Dietary Supplement

Two capsules to be taken twice daily, one hour before meals

| Active Ingredients | |
|---|---|
| Chondroitin sulfate | 300 mg |
| Glucosamine sulfate | 300 mg |
| Quercetin | 300 mg |
| S-adenosylmethionine | 100 mg |
| extra virgin kernel seed olive oil | 900 mg |

Hypo-allergenic. Free from: artificial colors or flavors, corn, milk products, preservatives, salt, starch, sugar, wheat or yeast.

Example 4

Composition of Formulation Three (ALGONOT-PROTECT, Reg. Mark)

Skin ointment or cream. Apply three times per day to affected areas.

| Active Ingredient | % by weight |
|---|---|
| Condroitin sulfate | 5 |
| Quercetin | 3 |
| Extra virgin kernel seed olive oil | 15 |

Example 5

Composition of Formulation Four (ALGONOT-ALLERGY, Reg. Mark)

Formulation Three plus diphenhydramine, 5% by weight.

Example 6

Composition of Formulation Five (ALGONOT-PERIO)

Mouth Wash

Chondroitin sulfate, 0.4 M

Optionally: D-glucosamine sulfate, 0.4M; quercetin, 0.3M; SAM 0.15M

In a standard mouth wash vehicle.

Example 7

Composition of Formulation Six (ALGONOT-DENTAL)

| Tooth paste | mg % |
|---|---|
| *Chondroitin sulfate | 5 |
| *Quercetin | 3 |

*In a standard tooth paste vehicle

Example 8

Composition of Formulation Seven (ALGONOT-SUNSCREEN)

| Active ingredients | mg % |
|---|---|
| Chondroitin sulfate | 5 |
| Quercetin | 3 |
| Sun screen (e.g., TiO2) | 5 |

I claim:

1. A composition with synergistic anti-inflammatory properties for use in conditions induced by inflammatory disease-causing biomolecules released from mast cells by the activation and degranulation of said mast cells, comprising a non-bovine proteoglycan and unrefined kernel olive oil, and one or more of D-hexosamine sulfate, a flavonoid, S-adenosyimethionine, and a histamine-1-receptor antagonist, in an appropriate excipient or vehicle for oral or topical administration.

2. The composition according to claim 1, wherein said sulfated proteoglycan is selected from the group consisting of non-bovine chondroitin sulfate, keratan sulfate, dermatan sulfate and hyaluronic acid.

3. The composition according to claim 2, wherein said chondroitin sulfate is derived from shark cartilage.

4. The composition according to claim 1, wherein said hexosamine sulfate is D-glucosamine sulfate.

5. The composition according to claim 1, wherein said flavone is selected from the group consisting of quercetin, myrisetin, genistein and kaempferol.

6. The composition according to claim 1, wherein said olive oil contains omega fatty acids and alpha-tocopherol.

7. The composition according to claim 1, said composition being for oral use, comprising 300 mg each of non-bovine chondroitin sulfate C, quercetin and D-glucosamine sulfate, in kernel olive oil.

8. The composition according to claim 7, further comprising 100 mg of S-adenosylmethionine.

9. The composition according to claim 1, wherein said inflammatory disease is arthritis and said composition is contained in an ointment or cream for topical application, comprising, in mg %, chondroitin sulfate 0.05; unrefined kernel olive oil, 1–5; and one or more of D-glucosamine sulfate, 0.05, and quercetin, 0.03.

10. The composition according to claim 9, further comprising diphenhydramine, 5 mg %.

11. A composition according to claim 1, said composition consisting of a mouth wash composition, comprising chondroitin sulfate, 0.4 M; unrefined kernel olive oil 0.5–1.5 mg %; and one or more of D-glucosamine sulfate, 0.4 M; and quercetin, 0.3 M, in a mouth wash vehicle.

12. A composition according to claim 1, said composition consisting of a tooth paste, comprising, in mg %, chondroitin sulfate, 0.05; and unrefined kernel olive oil, 1–5, and one or more of D-glucosamine sulfate, 0.05; and quercetin, 0.03; in a tooth paste vehicle.

13. A composition according to claim 1, said composition consisting of a sunscreen composition, comprising, in mg %, chondroitin sulfate, 0.05, and unrefined kernel oil, 1–5; and one or more of D-glucosamine sulfate, 0.05; quercetin, 0.03; and titanium dioxide, 1–5; in a sun screen vehicle.

14. A method of treating a subject suffering from am inflammatory disease, wherein said inflammatory disease results from biomolecules secreted from activated and degranulated mast cells, said inflammatory disease being selected from the group consisting of osteoarthritis, cancer, fibromyalgia, atherosclerosis, inflammatory bowel disease, interstitial cystitis, irritable bowel syndrome, migraines, angina, chronic prostatitis, eczema, arthritis, multiple sclerosis, psoriasis, sun burn, and periodontal disease, comprising the step of administering to said subject an effective amount of a composition according to claim 1.

15. The composition according to claim 1, wherein said histamine-1-receptor antagonist is diphenhydramine.

16. The composition according to claim 1, wherein said inflammatory disease is arthritis and said composition is designed for oral administration, comprising non-bovine chondroitin sulfate, quercetin, D-glucosamine sulfate, and unrefined kernel olive oil.

17. The composition according to claim 9, comprising, in mg %, chondroitin sulfate, 0.05; D-glucosamine sulfate, 0.05; quercetin, 0.03; and, unrefined kernel olive oil, 1–5.

18. The composition according to claim 1 for oral use in allergic conditions, comprising chondroitin sulfate, a flavonoid selected from the group consisting of quercetin, myricetin and kaempferol, and said kernel olive oil.

19. The composition according to claim 18, comprising 200 mg each of chondroitin sulfate and kaempferol and said kernel olive oil.

20. The composition according to claim 18, comprising chondroitin sulfate and myricetin and said kernel olive oil.

21. The composition according to claim 20, supplemented with a histamine-1-receptor antagonist.

22. The composition according to claim 21, wherein said antagonist is diphenhydramine.

23. The composition according to claim 1, wherein said inflammatory disease is cancer and wherein said composition is designed for oral use, comprising 25–50 mg of genistein and 150–300 mg of quercetin, and said kernel olive oil.

24. The composition according to claim 1, wherein said inflammatory disease is atherosclerosis with or without myocardial ischemia, comprising 100–300 mg each of chondroitin sulfate, myricetin and S-adenosylmethionine, and said kernel olive oil, in a vehicle for oral use.

25. The composition according to claim 1, wherein said inflammatory disease is interstitial cystitis, said composition comprising 100–300 mg of chondroitin sulfate, 100–300 mg of hyaluronic acid, and 200–400 mg quercetin, and said kernel olive oil, in a vehicle for oral use.

26. The composition according to claim 1, wherein said inflammatory disease is prostatitis, said composition comprising 100–200 mg of chondroitin sulfate, 100–200 mg hyaluronic acid and 200–400 mg of quercetin, and said kernel olive oil, in a vehicle for oral use.

27. The composition according to claim 1, wherein said inflammatory disease is multiple sclerosis, said composition comprising 100–300 mg each of chondroitin sulfate, myricetin and S-adenosylmethionine, and said kernel olive oil, in a vehicle for oral use.

* * * * *